United States Patent [19]

Ibaraki

[11] Patent Number: 5,885,832
[45] Date of Patent: Mar. 23, 1999

[54] HUMAN LENS EPITHELIAL CELL LINE

[75] Inventor: Nobuhiro Ibaraki, Kawachi-gun, Japan

[73] Assignee: Senju Pharmaceutical Co., Ltd., Osaka, Japan

[21] Appl. No.: 831,964

[22] Filed: Apr. 2, 1997

Related U.S. Application Data

[63] Continuation-in-part of Ser. No. 624,062, Mar. 29, 1996, abandoned.

[51] Int. Cl.$^6$ ..................................................... C12N 5/08
[52] U.S. Cl. ............................................................ 435/371
[58] Field of Search ................................ 435/371, 172.1, 435/172.2, 320.1, 378, 7.21

[56] References Cited

U.S. PATENT DOCUMENTS

| | | | |
|---|---|---|---|
| 5,514,552 | 5/1996 | Rosner et al. | 435/7.21 |
| 5,529,920 | 6/1996 | Cole et al. | 435/6 |
| 5,643,782 | 7/1997 | Andley et al. | 435/371 |

OTHER PUBLICATIONS

U. Andley et al., *Investigative Ophthalmology & Visual Science*, 35(7), 3094–3102 (1994).

*Primary Examiner*—James Ketter
*Assistant Examiner*—Irem Yucel
*Attorney, Agent, or Firm*—Wenderoth, Lind & Ponack, L.L.P.

[57] ABSTRACT

A human lens epithelial cell line capable of expressing an exogeneous immortalizing gene, which is established without infecting with a live virus. A method for producing the human lens epithelial cell line, which comprises transfecting human lens epithelial cells with an expression vector functionally carrying an exogeneous immortalizing gene, and subculturing said cells in a medium. The above-mentioned human lens epithelial cell line wherein the cells proliferate in a temperature sensitive manner. A method for producing a temperature sensitive human lens epithelial cell line, which comprises transfecting human lens epithelial cells with an expression vector functionally carrying an exogeneous immortalizing gene, and subculturing said cells in a medium. Since the human lens epithelial cell line of the present invention is free of infection with a live virus, the cells are useful as biomaterials. Moreover, since the temperature sensitive human lens epithelial cell line of the present invention stops proliferation at about 36° C. or above, it may be used as a biomaterial for regenerating a human lens.

13 Claims, 8 Drawing Sheets

HUMAN LENS EPITHELIAL CELL LINE

This is a continuation-in-part of U.S. patent application Ser. No. 08/624,062, filed Mar. 29, 1996 now abandoned.

BACKGROUND OF THE INVENTION

1. Field of the Invention

The present invention relates to a human lens epithelial cell line and a production method thereof.

2. Description of Related Art

Various studies have been made to clarify cataract which is the main cause of blindness. A truly efficacious agent for prophylaxis and treatment of cataract has not been developed, and the most effective therapy is currently a surgical extraction of an opacified lens and implantation of an artificial lens (intraocular lens). Artificial lenses are prepared from polymethylmethacrylate, silicone and the like, and may lack bioavailability and biocompatibility, causing ocular inflammation, edema and the like at graft site. Such artificial lenses are under development, which includes, for example, monofocal lenses and multifocal lenses capable of acquiring sight on both far view and near view. Nonetheless, artificial lenses are markedly different in precision, shape and the like from inborn lenses having authentic amplitude of accommodation.

While artificial lenses prepared from inborn materials may be of interest, the peculiarity of the lens in that it is composed of transparent and refractive tissues has hindered the development of artificial lenses made from inborn materials.

Under the circumstances, the present inventor took note of grafting human-originated lens epithelial cells in place of an artificial lens and allowing proliferation and differentiation of said cells at the graft site, thereby to regenerate human lens to cure cataract.

The lens consists of a single cell species inclusive of lens epithelial cells and lens fiber cells resulting from differentiation and elongation of the lens epithelial cells, with its entirety covered by a lens capsule made by collagen in the main. Inasmuch as the lens fiber cells have been known to have lost proliferation potency and disintegrates DNA and nucleus as they become fibrous, lens epithelial cells alone can be actually grafted for regeneration of a lens. The lens epithelial cells of many animal species have been known to differentiate into lens fiber cells in vitro, and have been used for elucidation of differentiation mechanism of cells and studies of cataract.

The human lens epithelial cells have noticeably low proliferation potency when compared to lens epithelial cells of animals such as cow and chicken. Furthermore, lens epithelial cells obtained from adult cataract patients or senile cataract patients are either substantially incapable of culture or barely proliferated even if they permit culture at all. While the lens epithelial cells obtained from infants can be cultured rather easily and the cultured cells can be subcultured several times, their proliferation potency is limited and cytomegalic cells and cell degeneration in a long-term subculture have been reported [Reddy V. N. et al., Exp. Eye Res., vol. 47, pp. 465–478 (1988), Ibaraki N. et al., Invest. Ophthalmol. Vis. Sci., vol. 36, pp. 2304–2312 (1995)]. Consequently, they are not suitable for practical use.

In view of this, it has been tried to make a human lens epithelial cell line. However, spontaneous human lens epithelial cell line has not been obtained. In the meantime, a human lens epithelial cell line has been successfully prepared by infecting human lens epithelial cells with adenovirus 12 in which large T antigen gene derived from simian virus 40 (SV40) known as an immortalizing gene has been incorporated [Andley U. P. et al., Invest. Ophthalmol. Vis. Sci., vol. 35, pp. 3094–3102 (1994)]. This method leads to the production of viruses from said cell line, since cells are infected with a live virus for the introduction of the immortalizing gene. It is an undeniable fact that a patient may be infected with the virus when such cells are grafted, even if the lens should be successfully regenerated.

In this method, moreover, a high efficiency of virus infection makes it difficult to isolate a cell line from a single clone, and the cell population produced as a result may possibly include heterogeneous cells from plural clones of different derivation.

Therefore, the establishment of a safe human lens epithelial cell line has been desired, which is useful for the physiological and biochemical studies of the lens and the development of medicaments for the prevention and treatment of lens diseases such as cataract, and which has homogeneous properties and does not cause viral infections when grafted to living organisms.

When a lens is regenerated by grafting human lens epithelial cells into the living body, proliferation of said human lens epithelial cells need to be stopped at a certain stage and the cells should proceed to differentiation into lens fiber cells. Hence, the establishment of a human lens epithelial cell line has been simultaneously desired, which is capable of terminating the proliferation of the cells at a desired time to induce differentiation.

It is therefore an object of the present invention to provide a monoclonal human lens epithelial cell line having homogeneous property, which is useful for the physiological and biochemical studies of the lens and the development of medicaments for the prevention and/or treatment of lens diseases such as cataract, and which is free of viral infection in patients who underwent cell grafting. Another object of the present invention is to provide the above-mentioned human lens epithelial cell line capable of easy control of cell proliferation.

SUMMARY OF THE INVENTION

The present inventor has succeeded in transfecting human lens epithelial cells with a plasmid expression vector, which plasmid functionally incorporating an immortalizing gene, thereby to impart infinite proliferation potency in vitro to lens epithelial cells without infecting with a live virus, whereby a human lens epithelial cell line permitting semi-permanent subculture has been established from a single clone. The present inventor has further succeeded in establishing a temperature sensitive human lens epithelial cell line wherein the proliferation can be controlled by adjusting proliferation temperature, specifically by introducing an immortalizing gene from a temperature sensitive mutant virus into human lens epithelial cells in the same manner.

Accordingly, the present invention provides the following.

(1) A human lens epithelial cell line capable of expression of an exogenous immortalizing gene, which has been established without infecting with a live virus, particularly, such human lens epithelial cell line capable of maintaining the following properties at least for 35 passages:
   i) absence of decreased proliferation rate,
   ii) being substantially free of cytomegalic or degenerating cells, iii) being genetically stable, and iv) being capable of producing α-crystallin.

(2) The human lens epithelial cell line capable of expression of an exogenous immortalizing gene of (1) above, which is established by transfecting human lens epithelial cells with an expression vector, specifically a plasmid vector, which vector functionally carrying an exogenous immortalizing gene, particularly an immortalizing gene from virus, more particularly SV40 large T antigen gene, and subculturing said cells in a medium.

(3) The human lens epithelial cell line capable of expression of an exogenous immortalizing gene of (1) or (2) above, wherein the cells are temperature sensitive in proliferation, particularly said cell line wherein the cells stop proliferation within 2 weeks at the latest at not less than about 36° C.

(4) The human lens epithelial cell line capable of expression of an exogenous immortalizing gene of (3) above, wherein the exogenous immortalizing gene is a temperature sensitive mutant gene.

(5) A method for producing the human lens epithelial cell line of (1) or (2) above, which comprises transfecting human lens epithelial cells with an expression vector functionally carrying an exogenous immortalizing gene, and culturing said cells in a medium.

(6) A method for producing the human lens epithelial cell line of (4) above, which comprises transfecting human lens epithelial cells with an expression vector functionally carrying a temperature sensitive mutant immortalizing gene, and subculturing said cells in a medium.

DETAILED DESCRIPTION OF THE INVENTION

The human lens epithelial cell line of the present invention contains an exogenous immortalizing gene and is a cell population from a single clone, which has acquired infinite in vitro proliferation potency as a result of expression of said immortalizing gene, and which is further characterized by the absence of infection with a live virus when introducing the immortalizing gene.

As used herein, by an immortalizing gene is meant a gene which immortalizes cells to impart infinite proliferation potency, and is exemplified by oncogenes such as c-myc and ras, adenovirus E1A, large T antigen genes derived from SV40 (SV40 large T antigen gene) and polyoma virus large T antigen gene.

As used herein, by exogenous immortalizing gene is meant an immortalizing gene introduced newly from outside a cell, which is not inherently possessed by human lens epithelial cells to be the origin of the human lens epithelial cell line of the present invention. Therefore, the exogenous immortalizing gene in the present invention includes, besides an immortalizing gene derived from a non-human species, for example, a human oncogene modified such that it is capable of expression in target cells; in other words, free of repressed expression as in normal endogenous human oncogene. The exogenous immortalizing gene in the present invention is preferably an immortalizing gene from a virus, and more preferably SV40 large T antigen gene.

The human lens epithelial cell line of the present invention is preferably established by transfecting human lens epithelial cells isolated from tissues with an expression vector functionally carrying the above-mentioned exogeneous immortalizing gene; "functionally" meaning that the gene can express in the target cells, and subculturing said cells in a suitable medium. Examples of the human lens epithelial cells include lens epithelium such as that obtained in ophthalmic surgery (e.g., cataract surgery and vitreous surgery). Particularly preferred is lens epithelium of infants obtained in vitreous surgery for the treatment of retinopathy of prematurity.

The lens epithelial cells can be obtained by releasing epithelial cells along with lens capsule from the removed lens tissues and treating same with EDTA and/or trypsin to release the lens capsule, whereby a dissociated single cell is obtained. The obtained free human lens epithelial cells are suspended in a suitable liquid medium containing fetal bovine serum or calf serum in a proportion of 10–20%, such as Eagle's minimum essential medium (EMEM), Dulbecco's modified EMEM, HAM medium F12 and Katsuta medium DM-160, and preincubated in a $CO_2$ incubator for 14–21 days. The resulting cells are subjected to transfection.

The expression vector to be used in the present invention is exemplified by a plasmid vector and a virus vector, with preference given to a plasmid vector. When a human virus genome is used as a vector, the gene is preferably made partly defective or mutated so that at least complete virus particles will not be produced in the cells into which said vector has been introduced.

For construction of an expression vector functionally carrying an exogenous immortalizing gene, the following method is typically used when an SV40 large T antigen gene is involved as the exogenous immortalizing gene.

To be specific, a DNA fragment containing an immortalizing gene, i.e., large T antigen gene, present in the early region of an SV40 genomic DNA is cleaved with suitable restriction enzymes, and inserted into a plasmid vector containing a promoter capable of expressing said gene in human cells. Examples of the promoter include SV40 early promoter, Rous sarcoma virus (RSV) promoter, MuMLV LTR and the like. When an SV40 early promoter is used, an immortalizing gene including the promoter may be cleaved out from an SV40 genomic DNA.

The plasmid vector is exemplified by pBR322 and pGEM. In addition, a terminator signal and a specific sequence enhancing the expression of SV40 large T antigen gene may be inserted at suitable positions in said vector. The immortalizing gene expression vector thus constructed is synthesized in large amounts in suitable hosts such as *Escherichia coli*, yeast and *Bacillus subtilis*, and subjected to the purification of said vector DNA by a conventional method. The vector DNA thus obtained is introduced into lens epithelial cells by an optional method conventionally used for the introduction, such as calcium phosphate coprecipitation method, microinjection, PEG method and electroporation.

The cells after transfection are cultured in a liquid medium such as EMEM, Dulbecco's modified EMEM, RAM medium F12 and Katsuta medium DM-160. The culture is performed under the conventional conditions. The medium is changed to a fresh medium every 2 or 3 days and the culture is subcultured when it achieved confluence. Culture is continued even after the cell proliferation stops, and the cells whichinitiated proliferation again are separated as monoclonal cells. The clone is separated as in the following. A small-sized round filter impregnated with trypsin and EDTA solution is gently placed on the clone to detach the cells from the culture dish onto the small filter.

The cloned cells which adhered to the small filter are placed in another culture dish together with the filter.

The human lens epithelial cell line obtained in the above can be cultured by a standard tissue culture technique. As the index of the cell proliferation potency, the cell population doubling level (PDL) calculated by the following equation can be used.

$$PDL = \log_{10}(N_i/N_0)/\log_{10} 2$$

wherein $N_i$ is the cell count after the ith passage of subculture and $N_0$ is the cell count at the initiation of the first passage of subculture.

The human lens epithelial cell line of the present invention stably maintains the following properties for not less than 35 passages, preferably 70 passages or more:

i) absence of decreased proliferation rate, ii) being substantially free of cytomegalic or degenerating cells, iii) being genetically stable, and iv) being capable of producing α-crystallin.

As used herein, "being substantially free of cytomegalic or degenerating cells" means that most of the cells as observed with a microscope show morphological characteristics of the original human lens epithelial cells, even if a part thereof might have been elongated. Moreover, "being genetically stable" means that the cells are devoid of changes made during subculture at least in the number of chromosomes and sex chromosomes. The incident of α-crystallin production indicates physiological properties as human lens epithelial cells.

The temperature sensitive human lens epithelial cell line of the present invention can be established by transfecting human lens epithelial cells with an expression vector containing an immortalizing gene expression cassette whose expression is temperature sensitive, and subculturing said cells in a suitable medium. Examples of the temperature sensitive immortalizing gene expression cassette to be used include a large T antigen structural gene of temperature sensitive mutant SV40. The temperature sensitive human lens epithelial cell line of the present invention preferably stops proliferation within 2 weeks at the latest at not less than about 36° C., and characteristically continues to proliferate stably at a lower temperature, preferably at about 33° C.

The cell line of the present invention is not produced by an infection with a live virus, but transfection with an expression vector containing an immortalizing gene. As such, at least complete virus particles are not produced in the cells, which means that grafting said cell line into human does not lead to a viral infection. Said cell line is obtained from a single clone to enjoy homogeneous properties. It can be a model cell useful for physiological and biochemical studies conventionally performed using nonuniform lens epithelial cells, such as elucidation of the etiology of cataract, regeneration of the lens, development of artificial lenses from biological materials and the like. Inasmuch as this cell line ensures stable supply, an improved accuracy of the evaluation of anti-cataract drugs can be expected. Moreover, the cell line of the present invention permits biosynthesis of lens specific proteins, α- and β-crystallins. Hence, the cells when produced in large amounts enable efficient production of these proteins. Moreover, since the temperature sensitive human lens epithelial cell line of the present invention can end the proliferation at a temperature near that of human eyes, it can be a promising candidate for graft cell for regeneration in vivo of a human lens.

The present invention is explained in more detail by way of the following Examples and Experimental Examples, to which the present invention is not limited. Note that the human lens epithelial cell line SRA 01/04 has been internationally deposited at the National Institute of Bioscience and Human-Technology Agency of Industrial Science and Technology, Ibaraki, Japan, since Mar. 8, 1996 under the deposit No. FERM BP-5454, and the temperature sensitive human lens epithelial cell line SRA 01/01 at said Institute since Mar. 7, 1997 under the deposit No. FERM BP-5858.

EXAMPLE 1

Preparation of plasmid pRSV-B-TAg containing SV40 large T antigen gene

The plasmid pRSV-B-TAg containing an SV40 large T antigen gene is obtained by introducing an RSV promoter and a large T antigen gene into a commercially available plasmid pGEM3Zf(+) (Promega).

Figure 1:
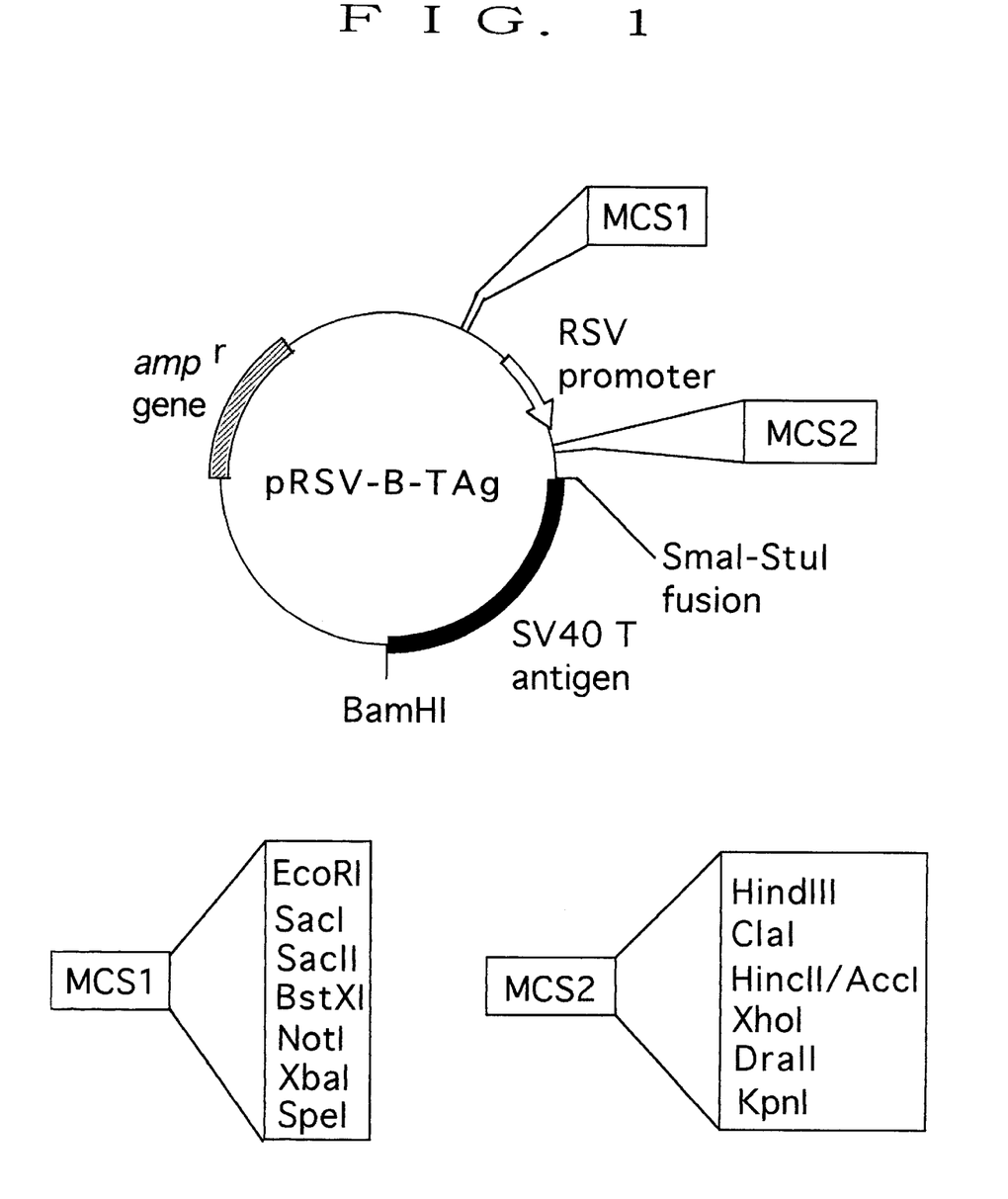
FIG. 1 shows a physical map of plasmid pRSV-B-TAg.

To be specific, the RSV promoter was prepared from a commercially available genomic DNA. This promoter was inserted into the SacI-KpnI site of plasmid pGEM3f(+). A 2657 bp fragment having large T antigen gene was cleaved out from a commercially available SV40 genomic DNA (Gibco) with restriction enzymes StuI and BamHI, which fragment was inserted into the SmaI-BamHI site of plasmid pGEM3Zf(+) to give the objective plasmid pRSV-B-TAg. The physical map of this plasmid pRSV-B-TAg is shown in FIG. 1.

The digestion of DNA, and isolation and ligation of DNA fragment for the construction of the plasmid as mentioned above were performed according to the method of Maniatis, T., et al, Molecular Cloning, A Laboratory manual, Cold Spring Harbor Laboratory (1982).

EXAMPLE 2

Preparation of human lens epithelial cell line

The lens epithelial cells were obtained from infants who underwent vitreous surgery for the treatment of retinopathy of prematurity. The anterior lens capsule having lens epithelial cells adhered thereto was subjected to stationary culture in Dulbecco's modified EMEM (Gibco) supplemented with 20(v/v) % fetal bovine serum (Gibco) but without antibiotics and antifungal agent (primary culture). The culture environment was 5(v/v) % $CO_2$, temperature 36.5° C. and humidity 100%, and the medium was changed 3 times a week. Approximately two weeks later, the cultures were confirmed to have achieved near confluence and the cells were detached and separated with 0.05(w/v) % trypsin and 0.02(w/v) % EDTA. The cells were subcultured in a culture dish at a density of 70±5 cells/mm². When the subculture (first passage) achieved near confluence, the cells were used for the introduction of plasmid DNA.

EXAMPLE 3

Tranfection

Then, the plasmid pRSV-B-TAg obtained in Example 1 was prepared into a DNA-calcium phosphate complex using a calcium phosphate transfection system (Gibco, calcium phosphate coprecipitation), and the complex solution was added to the above-mentioned human lens epithelial cell subculture in an amount that made the DNA amount 5 $\mu g/5 \times 10^5$ cells. The cultures were incubated for about 24 hours under the conditions used before the introduction of DNA, and the opacified solution of the DNA-calcium phosphate complex was removed, which was followed by continued culture. When the cultures achieved confluence, the cells were subcultured. The cells were continuously cultured even after the proliferation of the cells stopped in passage 3. The clones were separated which initiated proliferation again at about 3 months from the introduction of the DNA. The clones were separated as in the following. That is, a small-sized filter impregnated with 0.05(w/v) % trypsin and 0.02(w/v) % EDTA solution was placed on the clones to detach the cells from the culture dish and attach same onto the small filter. The cloned cells which adhered to the small filter were placed in another culture dish together with the filter.

The isolated clones were cultured separately. The expression of the immortalizing gene was confirmed by the fluorescent antibody method. The clones wherein human-originated isozyme phenotypes were confirmed on electrophoresis, and the clones wherein production of α- or β-crystallin, which are specific proteins of lens epithelial cells, was confirmed by Western blot analysis, were selected and subcultured as human lens epithelial cell lines. The fluorescent antibody method, isozyme analysis and Western blot analysis are to be described in detail in Experimental Examples 1, 2 and 3 below.

EXAMPLE 4

Subculture of the cells

Figure 2:
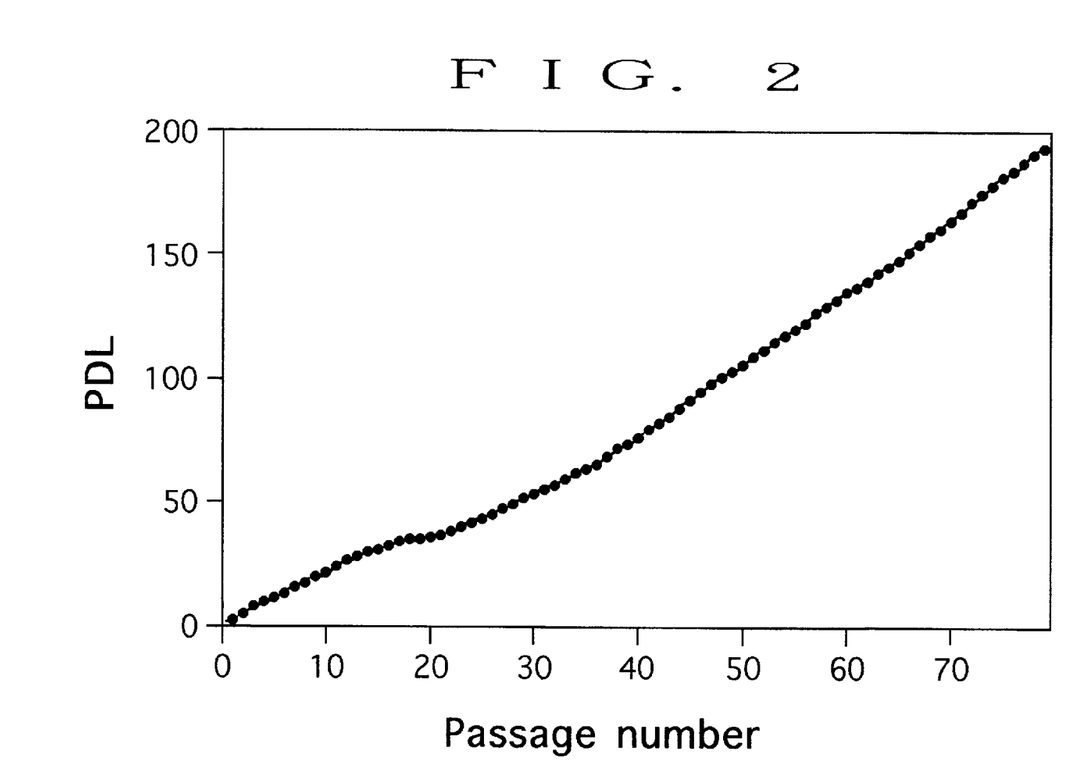
FIG. 2 shows the population doubling level (PDL) of human lens epithelial cell line SRA 01/04.

The cells of human lens epithelial cell line (passage 3, named SRA 01/04 strain) obtained in Example 3 were cultured through passage 79 under the same conditions as in Example 2. The final cell density in each passage was determined by counting the cells with a calculating board, based on which PDL was calculated. As a result, the cultures showed stable proliferation potency up to passage 79 as shown in FIG. 2.

Figure 3:
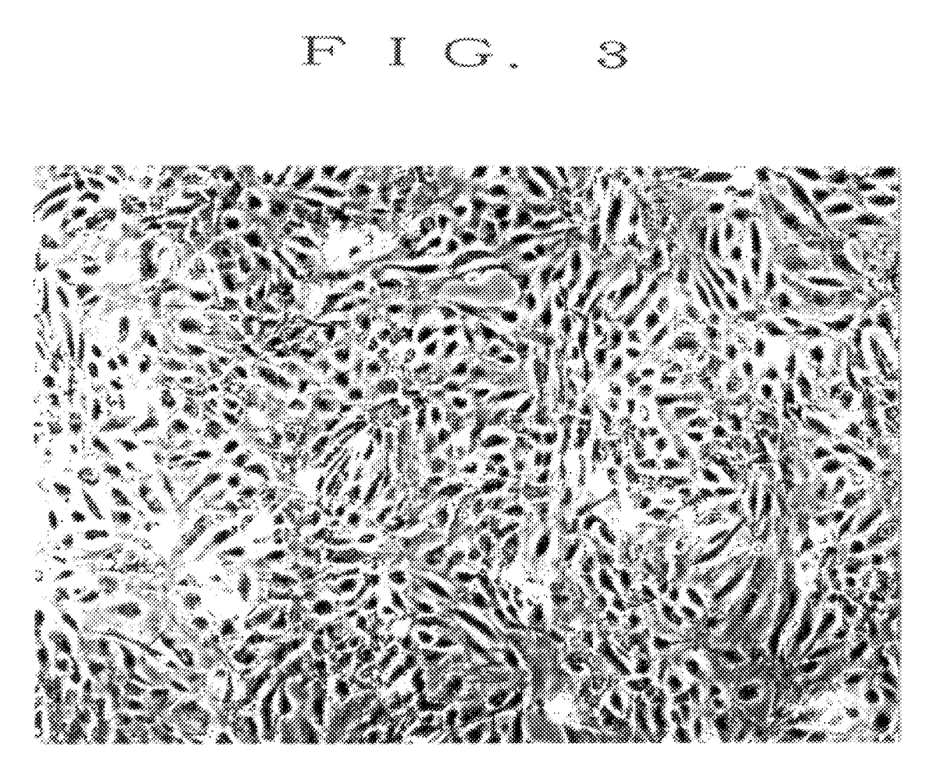
FIG. 3 is a photograph in a phase-contrast microscope showing human lens epithelial cell line SRA 01/04 in passage 26.

Using an inverted phase-contrast microscope, morphological changes of the cells at every passage were observed. The morphology of the cells in passage 26 is shown in FIG. 3. The cells consisted of a single layer, and mostly showed a morphology of epithelial cells, though elongated cells were partly observed. No cytomegalic or degenerating cells were found up to passage 79.

Experimental Example 1

Expression of SV40 large T antigen

Figure 4:
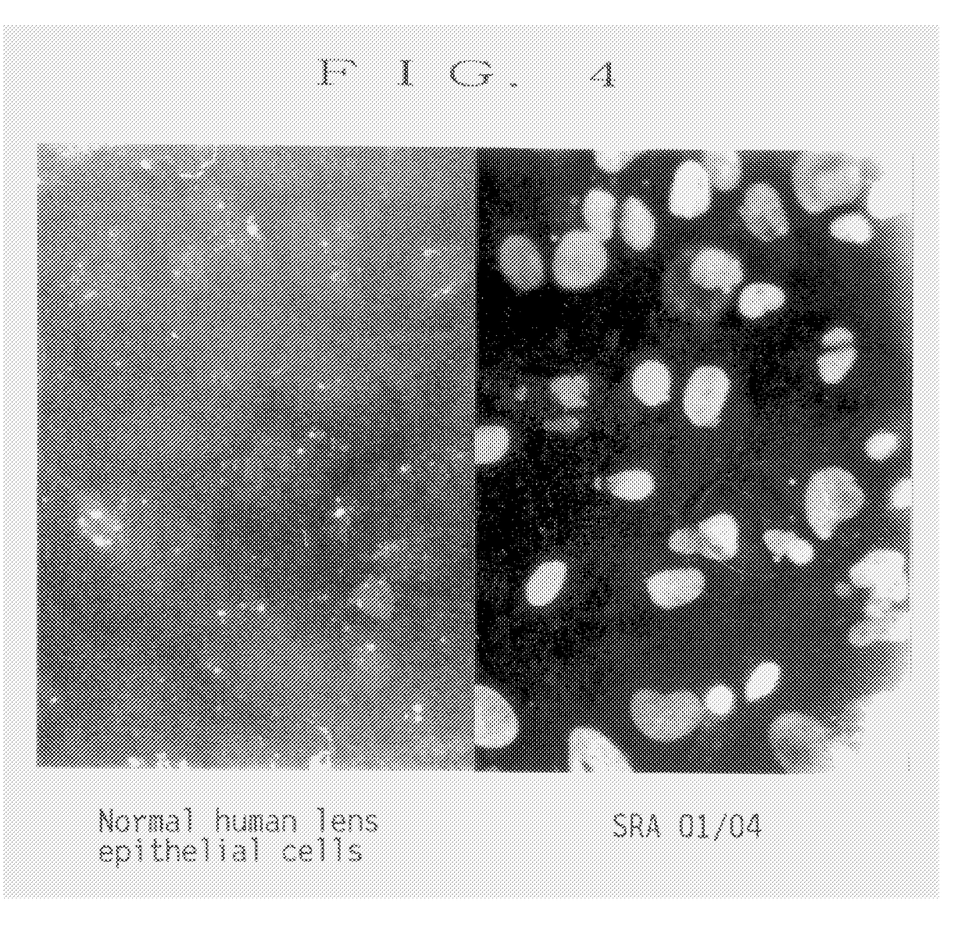
FIG. 4 is a fluorescent microscopic photograph of human lens epithelial cell line SRA 01/04 in passage 11, showing expression of SV40 large T antigen.

The introduction of immortalizing gene into the cells was confirmed by the fluorescent antibody method. To be specific, the cells were labeled by the fluorescent antibody method using mouse anti-SV40 large T antigen antibody (ATCC, antibody No. PAB101) as a primary antibody and FITC (fluorescein isothiocyanate)-labeled goat anti-mouse IgG as a secondary antibody. The photograph of the labeled cell line in a fluorescent microscope is shown in FIG. 4. From this photograph, the expression of the introduced immortalizing gene was confirmed.

Experimental Example 2

Isozyme analysis

The cells of the obtained cell line were analyzed for isozyme by the following method using a commercially available kit. The isozyme type was determined with regard to LDH, G6PDH, PGM1, PGM3, ESD, AK-1 and GLO-1.

To be specific, the cells were detached from the dish using 0.05(w/v) % trypsin and 0.02(w/v) % EDTA. An enzyme extracting solution (0.1 ml) [5 mM Tris-HCl (pH 7.5), 1 mM EDTA, 2% Triton X-100] was added to extract the enzyme on ice. Then, the extract was electrophoresed on an agarose gel to identify the origin of the cells using a commercially available kit (Coning, Authenti Kit). After the electrophoresis, a substrate solution was flown on the agarose gel to allow color development. As a control, enzyme standard products extracted from human-originated Hela cells and mouse-originated L929 cells were subjected to the same treatments to determine the origin of the cells by the comparison of the band patterns. The obtained band patterns coincided with those of normal human cells with respect to every enzyme (see Table 1). Accordingly, the origin of the cells was confirmed to be not other animals such as mouse but human.

TABLE 1

| | | Isozyme phenotypes | | | | |
|---|---|---|---|---|---|---|
| LDH | G6PDH | PGM1 | PGM3 | ESD | AK-1 | GLO-1 |
| human | B | 1–2 | 1 | 1 | 1 | 2 |

Experimental Example 3

Chromosomal analysis

Figure 5:
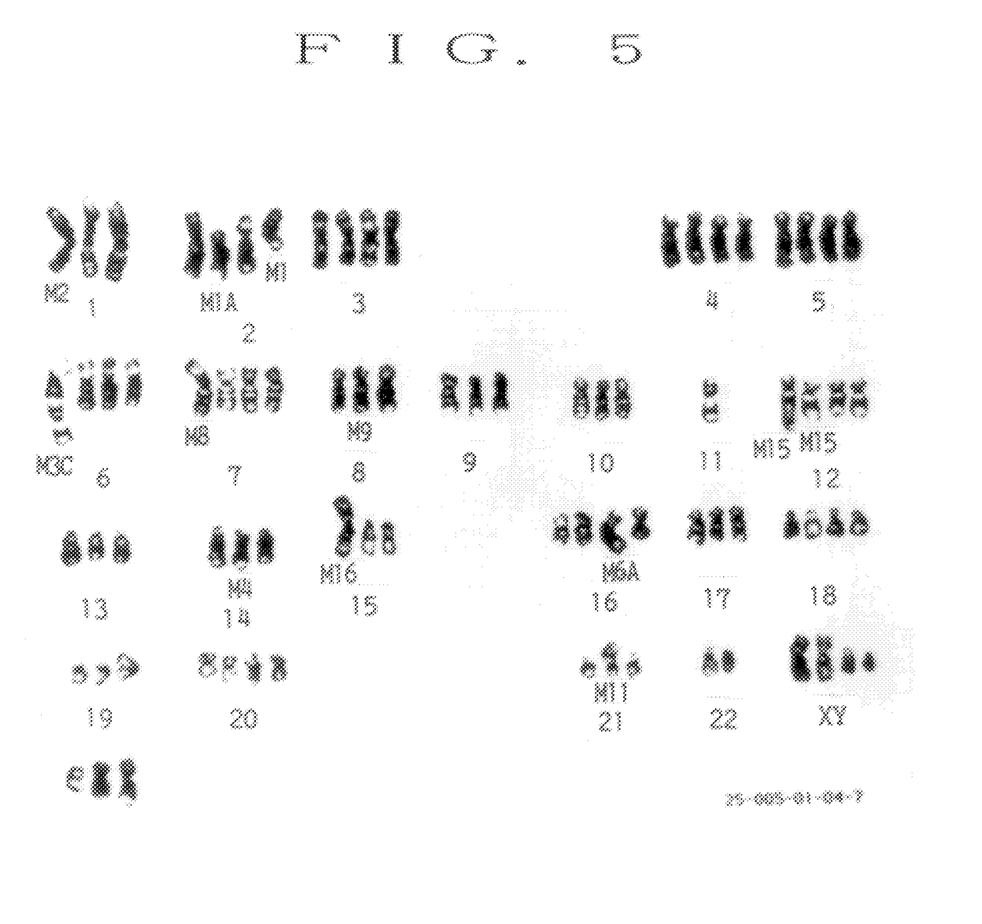
FIG. 5 is a photograph showing the karyotype of human lens epithelial cell line SRA 01/04 in passage 7.

The cells of the cell line of the present invention were treated with colchicine to stop cell division. The cells were spread on a slide glass by the squash method, dried with air, immobilized with ethanol:acetic acid (3:1), stained with orcein acetate and observed in an optical microscope. The chromosomal analysis (karyotype) of the cells is shown in FIG. 5, and the number of chromosomes and sex chromosomes are shown in Table 2.

The number of chromosomes did not show a diploid inherent to normal human but tetraploid peculiar to the cells of the cell line of the present invention (immortalized cells). The sex chromosomes were XXY/XXYY indicating male, which is consistent with the fact that the original cells of the cell line were obtained from male infants.

TABLE 2

| Chromosome count 2N = 46 | |
|---|---|
| Chromosome count | Number of metaphases |
| 72–87 | 88 |
| 2X (72–87) | 12 |

(sex chromosome: XXY/XXYY)

Experimental Example 4

Confirmation of α- and β-crystallin production by the cell line

The cells were dissolved in SDS-loading buffer [final concentration 50 mM, Tris-HCl (pH 6.8), 100 mM dithiothreitol, 2% SDS, 10% glycerol and 0.1% BPB] and subjected to SDS polyacrylamide electrophoresis (2% SDS, 5% PAG) according to the method of Laemmli. Then, Western blotting was performed by a conventional method using rabbit anti-α-crystallin antibody and mouse anti-β-crystallin antibody as probes.

Figure 6:
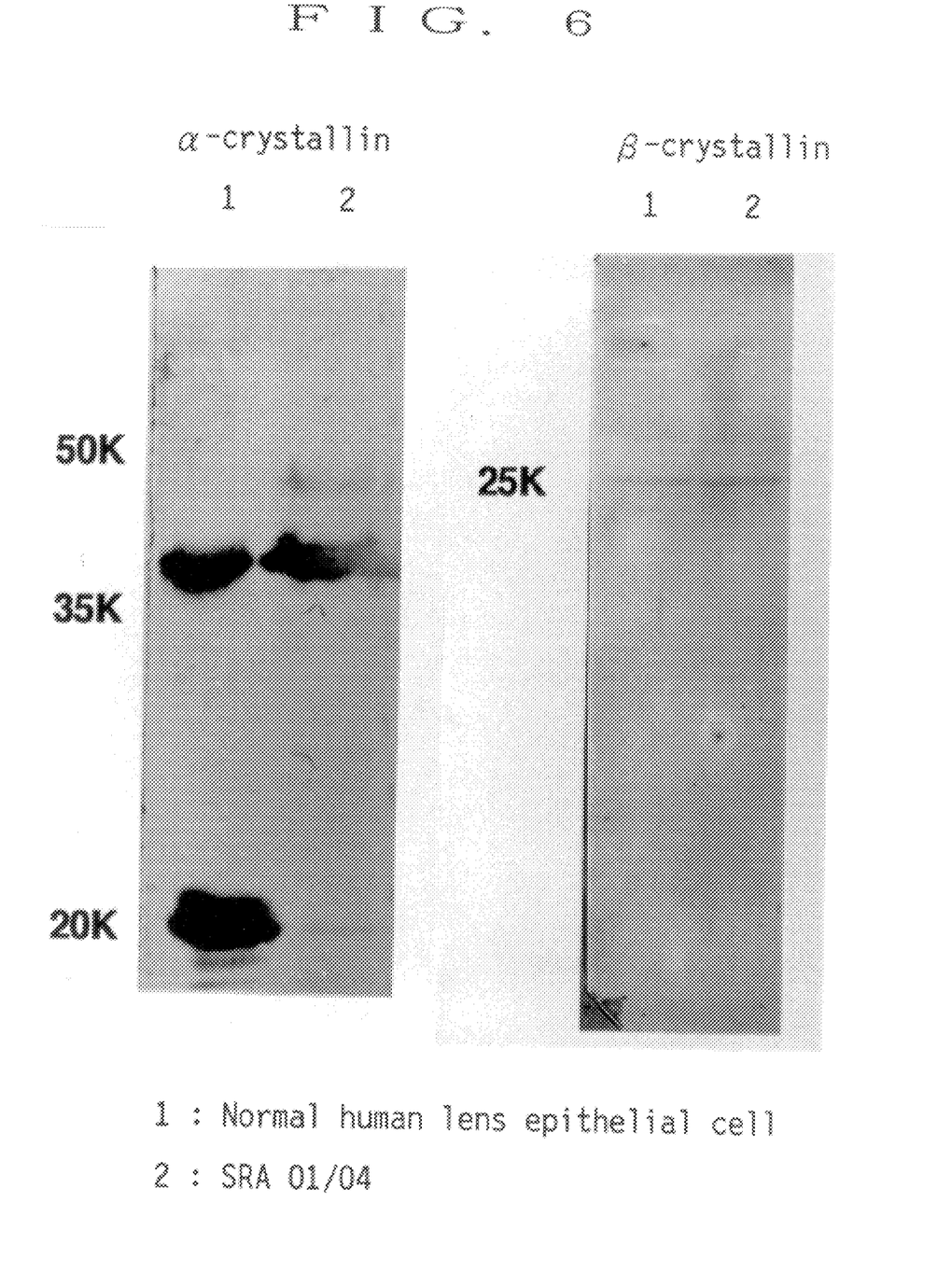
FIG. 6 shows the Western blot analysis of human lens epithelial cell line SRA 01/04 in passage 11, showing production of α-crystallin and β-crystallin.

The detection of α- and β-crystallins by the Western blot analysis is shown in FIG. 6. The results reveal the production of the lens specific proteins α- and β-crystallins by the cells of the cell line of the present invention, thereby suggesting that the cells were lens epithelial cells.

EXAMPLE 5
Establishment of temperature sensitive human lens epithelial cell line A full length genomic DNA of temperature sensitive mutant SV40 (tsA58) was digested with BamHI and ligated to pBR322 also digested with BamHI to give a plasmid vector. The digestion of DNA, isolation and ligation of DNA fragments and the like for construction of the above-mentioned plasmid followed the method of Maniatis, T. et al., Molecular Cloning, A Laboratory Manual, Cold Spring Harbor Laboratory (1982).

Figure 7:
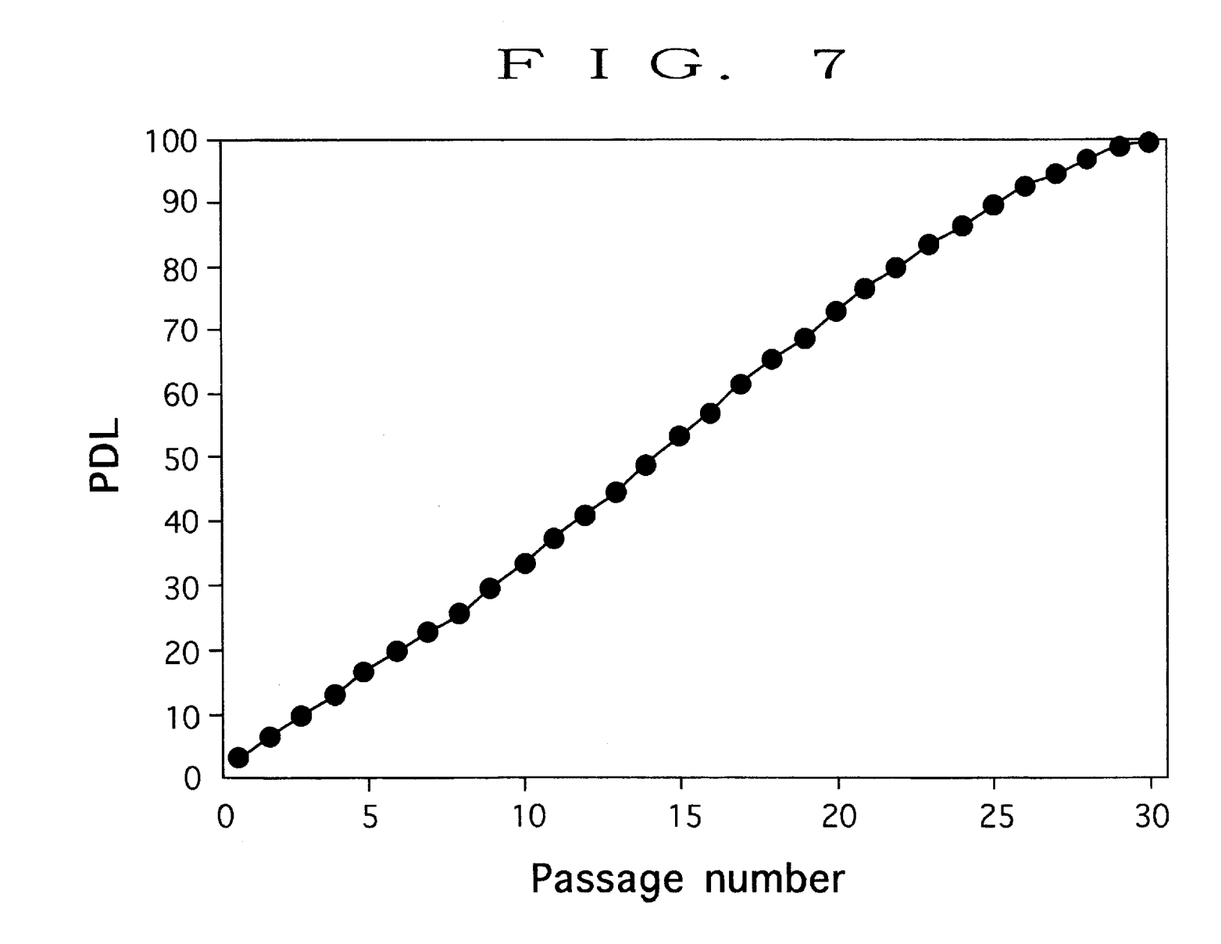
FIG. 7 shows PDL of temperature sensitive human lens epithelial cell line SRA 01/01.

Then, the free human lens epithelial cells obtained in Example 2 were tranfected with the above-mentioned plasmid vector in the same manner as in Example 3 and subcultured through passage 30 in the same manner as in Example 1 except that the cells were cultured at 33° C. (the cell line was named SRA 01/01 strain). In the same manner as in Example 4, PDL was calculated. As a result, stable proliferation potency was confirmed at passage 30 as shown in FIG. 7. Using an inverted phase-contrast microscope, morphological changes of the cells at every passage were observed. The cell line showed morphology characteristic of lens epithelial cells and no cytomegalic or degenerating cells were found at passage 30.

In the same manner as in Experimental Example 2, isozymes were analyzed. Every isozyme analyzed matched well with normal human cells (Table 3). It was therefore confirmed that said cell line was derived from human.

In the same manner as in Experimental Example 3, said cell line was subjected to chromosomal analysis. As a result, chromosomal count showed hypotetraploid (Table 4). The sex chromosome was XXYY and matched well with regard to the sex chromosome, since this cell line was derived from a male infant.

Further, in the same manner as in Experimental Example 4, production of α- and β-crystallins was examined. As a result, this cell line was confirmed to have produced both crystallins.

TABLE 3

| Isozyme expression type of SRA 01/01 | | | | | | | |
|---|---|---|---|---|---|---|---|
| LDH | G6PD | PGM1 | PGM3 | ESD | Me-2 | AK-1 | GLO-1 |
| human | B | 1-2 | 1 | 1-2 | 1-2 | 1 | 1-2 |

TABLE 4

| chromosomal count | cell count |
|---|---|
| 84–88 | 96 |
| 2 × (84–88) | 4 |

(sex chromosome: XX/YY)

Figure 8:
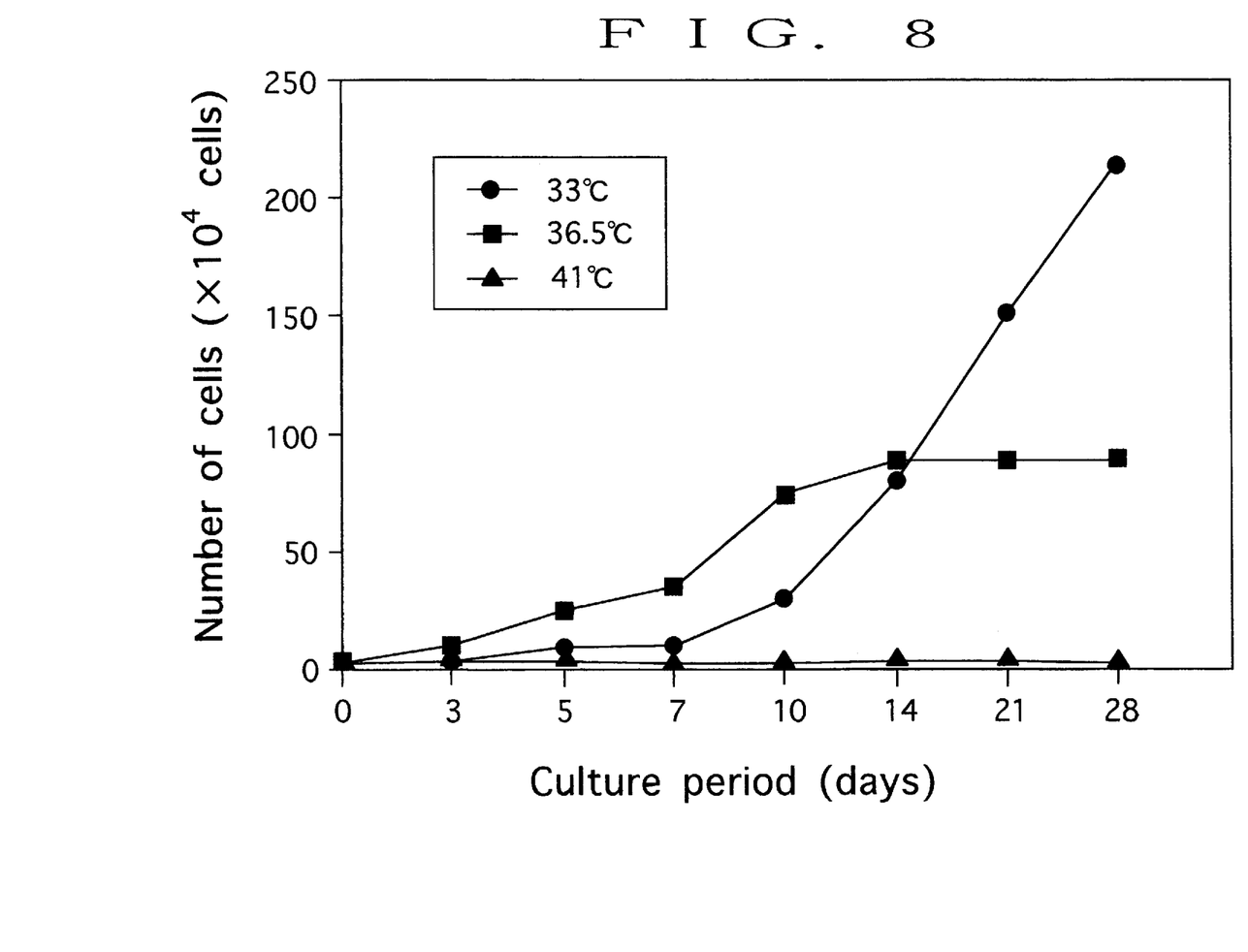
FIG. 8 shows proliferation curves of temperature sensitive human lens epithelial cell line SRA 01/01 at various culture temperatures.

Experimental Example 5
Confirmation of temperature sensitivity of temperature sensitive human lens epithelial cell line A part of the SRA 01/01 cells obtained in Example 5 was divided into three groups and cultured at 33° C., 36.5° C. and 41° C., respectively, wherein other culture conditions followed those in Example 1. The results are shown in FIG. 8. The cells stably proliferated at 33° C. for 4 weeks, whereas at 36.5° C., the proliferation stopped in about 2 weeks. The proliferation potency was completely lost at 41° C. From the above results, this cell line was confirmed to be a temperature sensitive human lens epithelial cell line.

The human lens epithelial cell line of the present invention is capable of supplying sufficient number of cells, and has a constant, continuous proliferation potency. Therefore, it can be advantageously utilized for the study of the etiology of cataract and development of an agent for the prophylaxis and/or treatment of cataract. In addition, since an immortalizing gene has been introduced by transfection, which obviates production of virus particles that may occur by a method including infection of a live virus, the cell line of the present invention can be used safely. Moreover, the cells are produced by a single clone and have homogeneous properties. Accordingly, the cells are useful for the physiological and biochemical studies of the lens and the studies of the differentiation mechanism of the cells. There is also a possibility that the cells can be used as biomaterials of an artificial lens.

Inasmuch as the temperature sensitive human lens epithelial cell line of the present invention stops proliferation at a temperature near that of human eyes, it can be a promising candidate for graft cells for in vivo regeneration of a human lens.

What is claimed is:

1. A human lens epithelial cell line which expresses an exogeneous immortalizing gene, which is established in the absence of a virus infection, and which possesses the following properties for at least 35 passages:
   i) absence of decreased proliferation rate,
   ii) substantially free of cytomegalic or degenerating cells,
   iii) genetically stable, and
   iv) production of α-crystallin.

2. The human lens epithelial cell line which expresses the exogeneous immortalizing gene of claim 1, which is established by transfecting human lens epithelial cells with a plasmid expression vector harboring a functional exogeneous immortalizing gene, and subculturing said cells in a medium.

3. The human lens epithelial cell line which expresses the exogeneous immortalizing gene of claim 1, wherein the exogenous immortalizing gene is isolated from a virus.

4. The human lens epithelial cell line which expresses the exogeneous immortalizing gene of claim 3, wherein the exogeneous immortalizing gene encodes an SV40 large T antigen.

5. The human lens epithelial cell line which expresses the exogeneous immortalizing gene of claim 1, wherein the cells grow in a temperature sensitive manner.

6. The human lens epithelial cell line which expresses the exogeneous immortalizing gene of claim 5, wherein the cells stop proliferation within 2 weeks at the latest at about 36° C. or above.

7. The human lens epithelial cell line which expresses the exogeneous immortalizing gene of claim 5, wherein the exogeneous immortalizing gene is a temperature sensitive mutant gene.

8. The human lens epithelial cell line which expresses the exogeneous immortalizing gene of claim 7, wherein the temperature sensitive mutant gene encodes a large T antigen from an SV40 temperature sensitive mutant.

9. A method for producing the human lens epithelial cell line which expresses the exogeneous immortalizing gene of claim 5, which comprises transfecting human lens epithelial cells with a plasmid expression vector harboring a functional temperature sensitive mutant immortalizing gene, and subculturing said cells in a medium.

10. The method of claim 9, wherein the temperature sensitive mutant immortalizing gene encodes a large T antigen from an SV40 temperature sensitive mutant.

11. A method for producing the human lens epithelial cell line which expresses the exogeneous immortalizing gene of claim 1, which comprises transfecting human lens epithelial cells with a plasmid expression vector harboring a functional exogeneous immortalizing gene, and subculturing said cells in a medium.

12. The method for producing the human lens epithelial cell line which expresses the exogeneous immortalizing gene according to claim 11, wherein the exogeneous immortalizing gene is isolated from a virus.

13. The method for producing the human lens epithelial cell line which expresses the exogeneous immortalizing gene according to claim 12, wherein the exogeneous immortalizing gene encodes an SV40 large T antigen.

* * * * *